(12) United States Patent
Ein-Gal

(10) Patent No.: US 7,460,636 B2
(45) Date of Patent: Dec. 2, 2008

(54) CT SCANNING SYSTEM WITH INTERLAPPING BEAMS

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 46 days.

(21) Appl. No.: 11/553,003

(22) Filed: Oct. 26, 2006

(65) Prior Publication Data

US 2008/0101533 A1  May 1, 2008

(51) Int. Cl.
*A61B 6/00* (2006.01)
(52) U.S. Cl. .................. 378/9; 378/4; 378/19; 378/901
(58) Field of Classification Search ...................... 378/9, 378/19, 901
See application file for complete search history.

(56) References Cited

U.S. PATENT DOCUMENTS

| 5,187,659 | A  | * | 2/1993  | Eberhard et al. | ................ | 378/9   |
| 2004/0213371 | A1 | * | 10/2004 | Bruder et al.   | ..................  | 378/9   |
| 2005/0281387 | A1 | * | 12/2005 | Kusch et al.    | ................  | 378/197 |

* cited by examiner

*Primary Examiner*—Edward J. Glick
*Assistant Examiner*—Mona M Sanei
(74) *Attorney, Agent, or Firm*—Dekel Patent Ltd.; David Klein

(57) ABSTRACT

A CT scanning system including a gantry operable to rotate about a rotation axis, and a plurality of X-ray imagers mounted on the gantry, each X-ray imager including a radiation source and a detector, wherein the radiation source is operative to emit a radiation beam (e.g., a cone beam) and the detector is positioned to receive the radiation beam so as to acquire partial projections set of an object through which the beams pass, wherein a union of the partial projections sets forms a projection set sufficient for CT reconstruction of the object.

13 Claims, 4 Drawing Sheets

CT SCANNING SYSTEM WITH INTERLAPPING BEAMS

FIELD OF THE INVENTION

The present invention relates generally to acquisition of CT projections using a multiplicity of beam imagers, such as cone beam imagers.

BACKGROUND OF THE INVENTION

In conventional computerized tomography (CT) for both medical and industrial applications, an x-ray fan beam and a linear array detector are employed to achieve two-dimensional axial imaging. The quality of these two-dimensional (2D) images is high, although only a single slice of an object can be imaged at a time. To acquire a three-dimensional (3D) data set, a series of 2D images are sequentially obtained in what is known as the "stack of slices" technique. One drawback to this method is that acquiring the 3D data set one slice at a time is an inherently slow process. There are other problems with this conventional tomographic technique, such as motion artifacts arising from the fact that the slices cannot be imaged simultaneously, and excessive exposure to x-ray radiation due to overlap of the x-ray projection areas.

Another technique for 3D computerized tomography is cone-beam x-ray imaging. In a system employing cone-beam geometry, an x-ray source projects a cone-shaped beam of x-ray radiation through the target object and onto a 2D area detector area. The target object is scanned, preferably over a 360° range, either by moving the x-ray source and detector in a scanning circle around the stationary object, or by rotating the object while the source and detector remain stationary. In either case, it is the relative movement between the source and object which accomplishes the scanning. Compared to the 2D "stack of slices" approach for 3D imaging, the cone-beam geometry is able to achieve 3D images in a much shorter time, while minimizing exposure to radiation. One example of a cone beam x-ray system for acquiring 3D volumetric image data using a flat panel image receptor is discussed in U.S. Pat. No. 6,041,097 to Roos, et al.

A significant limitation of existing cone-beam reconstruction techniques occurs, however, when the projection of the object being imaged is larger than the field-of-view of the detector, which is a quite common situation in both industrial and medical imaging applications. In this situation, some measured projections contain information from both the field of view of interest and from other regions of the object outside the field of view. The resulting image of the field of view of interest is therefore corrupted by data resulting from overlying material.

Several approaches have been proposed for imaging object projections larger than the field-of-view of the imaging system. U.S. Pat. No. 7,108,421 to Gregerson et al., the disclosure of which is incorporated herein by reference, describes a method for utilizing an under-sized detector to acquire CT data by stepwise moving said detector and thus sequentially accumulating sufficient projections for reconstruction. The system includes a source that projects a beam of radiation in a first trajectory; a detector located a distance from the source and positioned to receive the beam of radiation in the first trajectory; an imaging area between the source and the detector, the radiation beam from the source passing through a portion of the imaging area before it is received at the detector; a detector positioner that translates the detector to a second position in a first direction that is substantially normal to the first trajectory; and a beam positioner that alters the trajectory of the radiation beam to direct the beam onto the detector located at the second position. The radiation source can be an x-ray cone-beam source, and the detector can be a two-dimensional flat-panel detector array. The system can be used to image objects having projections larger than the field-of-view of the detector by translating the detector array to multiple positions, and obtaining images at each position, resulting in an effectively large field-of-view using only a single detector array having a relatively small size. A beam positioner permits the trajectory of the beam to follow the path of the translating detector, which permits safer and more efficient dose utilization, as generally only the region of the target object that is within the field-of-view of the detector at any given time will be exposed to potentially harmful radiation.

SUMMARY OF THE INVENTION

The present invention seeks to provide a system and method for acquisition of CT projections using a multiplicity of cone beam imagers, each one incorporating an x-ray source and an under-sized detector, as is described more in detail hereinbelow.

There is provided in accordance with an embodiment of the present invention a CT scanning system including a gantry operable to rotate about a rotation axis, and a plurality of X-ray imagers mounted on the gantry, each X-ray imager including a radiation source and a detector, wherein the radiation source is operative to emit a radiation beam (e.g., a cone beam) and the detector is positioned to receive the radiation beam so as to acquire partial projections set of an object through which the beams pass, wherein a union of the partial projections sets forms a projection set sufficient for CT reconstruction of the object.

The at least one partial projection set may overlap part of another sub-image projection set. The partial projection sets may include projections of axial cylindrical object shells, and the object shells may include an innermost shell and an outermost shell relative to the rotation axis.

In accordance with an embodiment of the present invention the gantry may include a rotator and a controller operable to control rotation of the rotator. A treatment device coupler may couple a coordinate system of a treatment device (e.g., a linear accelerator) to a coordinate system of the CT scanning system. A gantry coupler may be operable to cause rotation of the gantry by coupling the gantry to a rotating gantry of a treatment device.

In accordance with an embodiment of the present invention a couch may be operable to cause translation of the object. A translation controller may be operable to control translation of the object. The translation controller may be operable to cause translation of the object during rotation of the gantry. The translation of the object may be generally parallel to the rotation axis.

There is also provided in accordance with an embodiment of the invention a method for CT scanning including emitting radiation beams from a plurality of radiation sources mounted on a rotatable gantry, and detecting the radiation beams with detectors positioned to receive the radiation beams, so as to acquire partial projections set of an object through which the beams pass, wherein a union of the partial projections sets forms a projection set sufficient for CT reconstruction of the object. The gantry may be rotated and the steps of emitting and detecting the radiation beams may be repeated.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
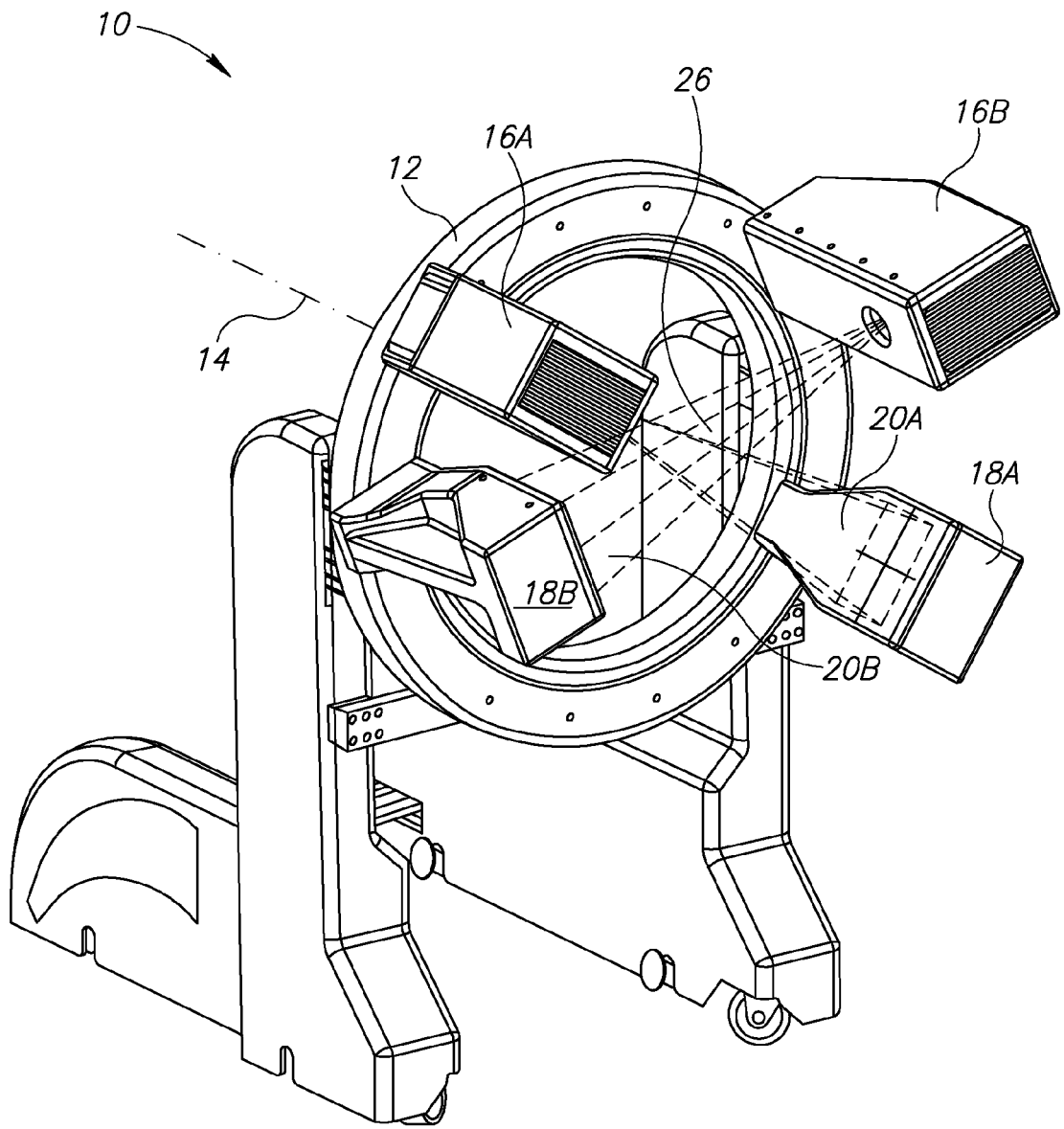
FIG. 1 is a simplified pictorial illustration of a CT scanning system, constructed and operative in accordance with an embodiment of the present invention.
Figure 2:
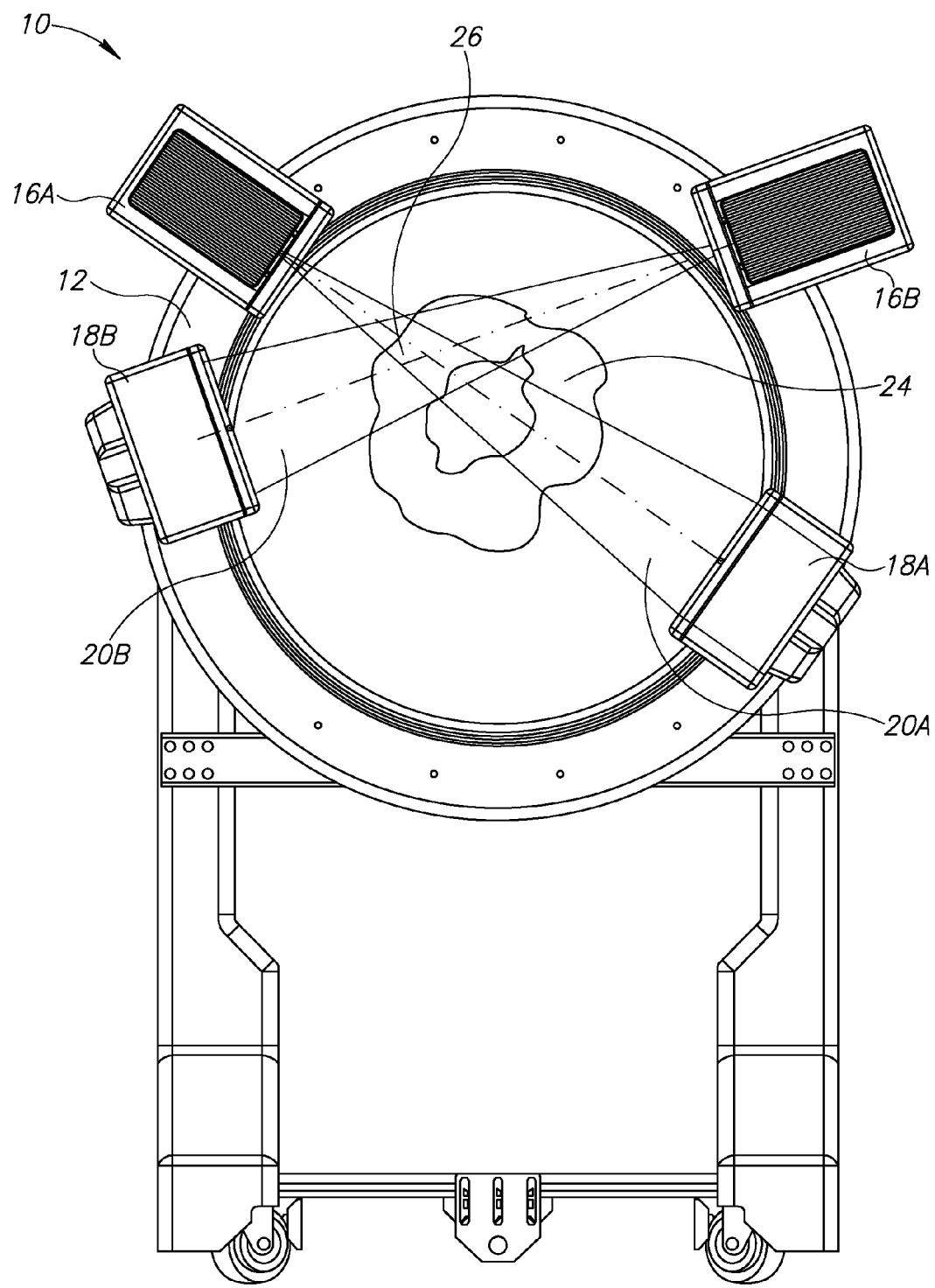
FIGS. 2 and 3 are simplified front-view illustrations of the CT scanning system of FIG. 1.
Figure 3:
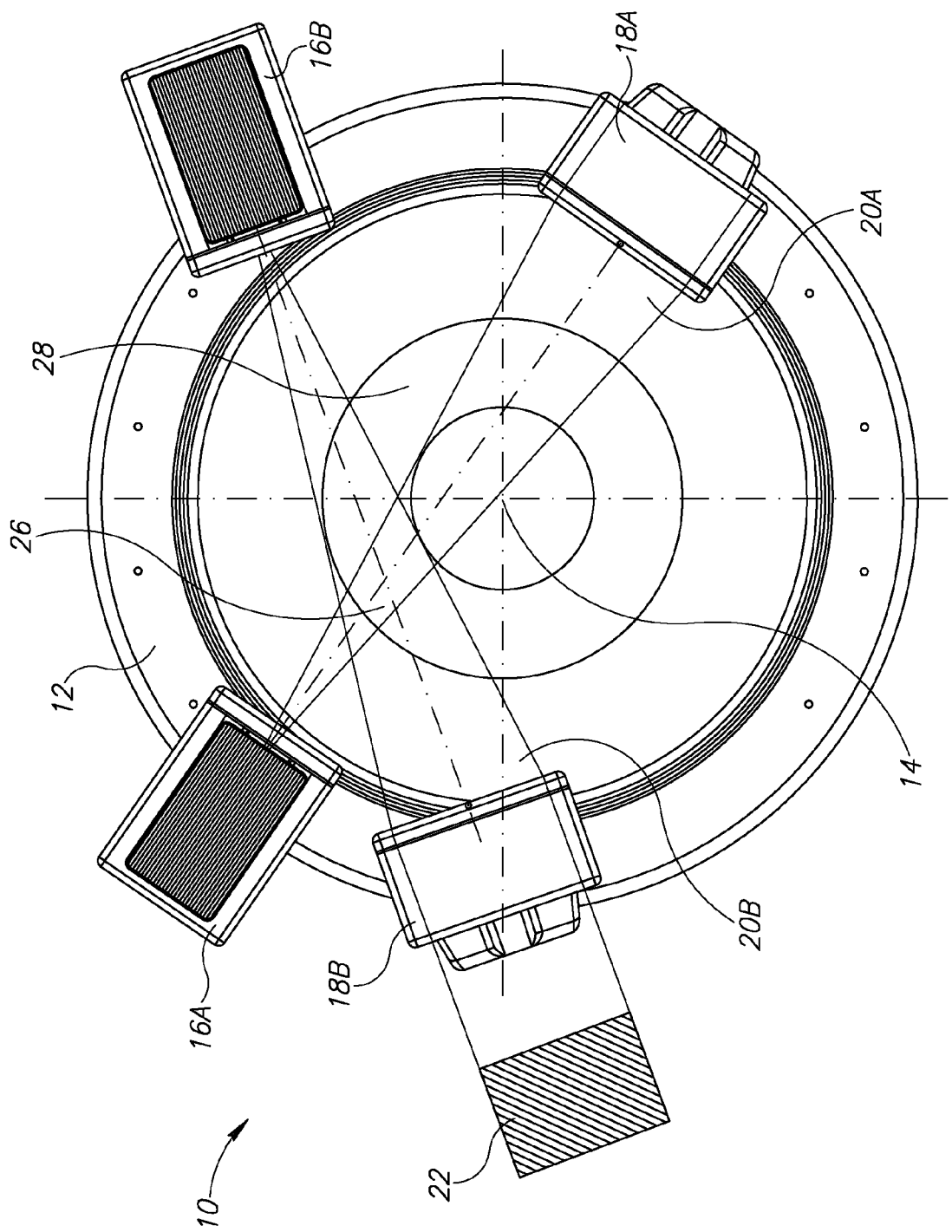

Reference is now made to FIGS. 1-3, which illustrate CT scanning system 10 constructed and operative in accordance with an embodiment of the present invention.

CT scanning system 10 may include a gantry 12, which may be rotated about a rotation axis 14. A plurality (two or more) of X-ray imagers may be mounted on gantry 12. Each X-ray imager includes a radiation source (16A and 16B in the figures) and a detector (18A/18B, respectively). The radiation source 16A/16B emits a radiation beam (20A or 20B, respectively), and the detector 18A/18B, which is located a distance from the radiation source 16A/16B, is positioned to receive the radiation beam 20A/20B. The radiation source 16A/16B may be, without limitation, an x-ray cone-beam source (in which case, the radiation beam is a cone beam), and the detector 18A/18B can be a two-dimensional flat-panel detector array, such as those described in U.S. Pat. No. 7,108,421.

FIG. 3 illustrates just one example of arranging the radiation sources 16A/16B and detectors 18A/18B, but it is emphasized that the invention is not at all limited to these exemplary dimensions. In the non-limiting embodiment of FIG. 3, detector 18A/18B is a two-dimensional flat-panel detector array with a pixel array of 768×575, measuring 220× 160 mm. The X-ray imagers may be mounted on gantry 12 by means of brackets, mechanical fasteners or any other convenient attachment means. Radiation sources 16A/16B and detectors 18A/18B are not aligned with the origin (isocenter) of the horizontal and vertical axes (which coincide with axis 14, which points perpendicular to the page of FIG. 3), but rather are off-axis from the isocenter. Radiation source 16A is positioned 55° counterclockwise from the upper vertical axis and detector 18A is positioned 55° counterclockwise from the lower vertical axis. Radiation source 16B is positioned 70° clockwise from the upper vertical axis and detector 18B is positioned 70° clockwise from the lower vertical axis. The distance from radiation source 16A/16B to detector 18A/18B is 875 mm. It is seen that the periphery of cone beam 20A intersects the isocenter, and at the isocenter, the periphery of cone beam 20A extends to a radius of 127.5 mm from the isocenter (i.e., an inner circle of 255 mm diameter). The periphery of cone beam 20B is tangent to the inner circle of 255 mm diameter, and the periphery of cone beam 20B extends to a radius of 250 mm from the isocenter (i.e., an outer circle of 500 mm diameter).

Each X-ray imager is thus operable to emit and capture radiation beams 20A/20B. Each detector 18A/18B acquires a partial projection set (one of which is shown and designated in FIG. 3 by reference numeral 22) of an object 24 (shown in FIG. 2). A union 26 of the partial projections sets forms a projection set sufficient for CT reconstruction of the object 24. Since the radiation beams 20A/20B overlap (intersect) each other, it is clear that at least one partial projection set overlaps part of another sub-image projection set.

In the embodiment shown in FIG. 3, the partial projection sets are orderly projections of axial cylindrical object shells 28. The shells 28 are bound by an innermost shell, defined by the periphery of cone beam 20A that extends to the inner circle (e.g., 255 mm diameter) relative to the rotation axis 14, and by an outermost shell, defined by the periphery of cone beam 20B that extends to the outer circle (e.g., 500 mm diameter) relative to the rotation axis 14.

The gantry 12 may include a rotator 30, such as a brushless servomotor, and a controller 32 operable to control rotation of the rotator 30. In this manner, the radiation beams 20A/20B may be generated around the rotation axis 14 to image the entire object or all of the object shells or any portion thereof. A processor may be provided that uses known CT reconstruction algorithms for reconstructing the object.

Figure 4:
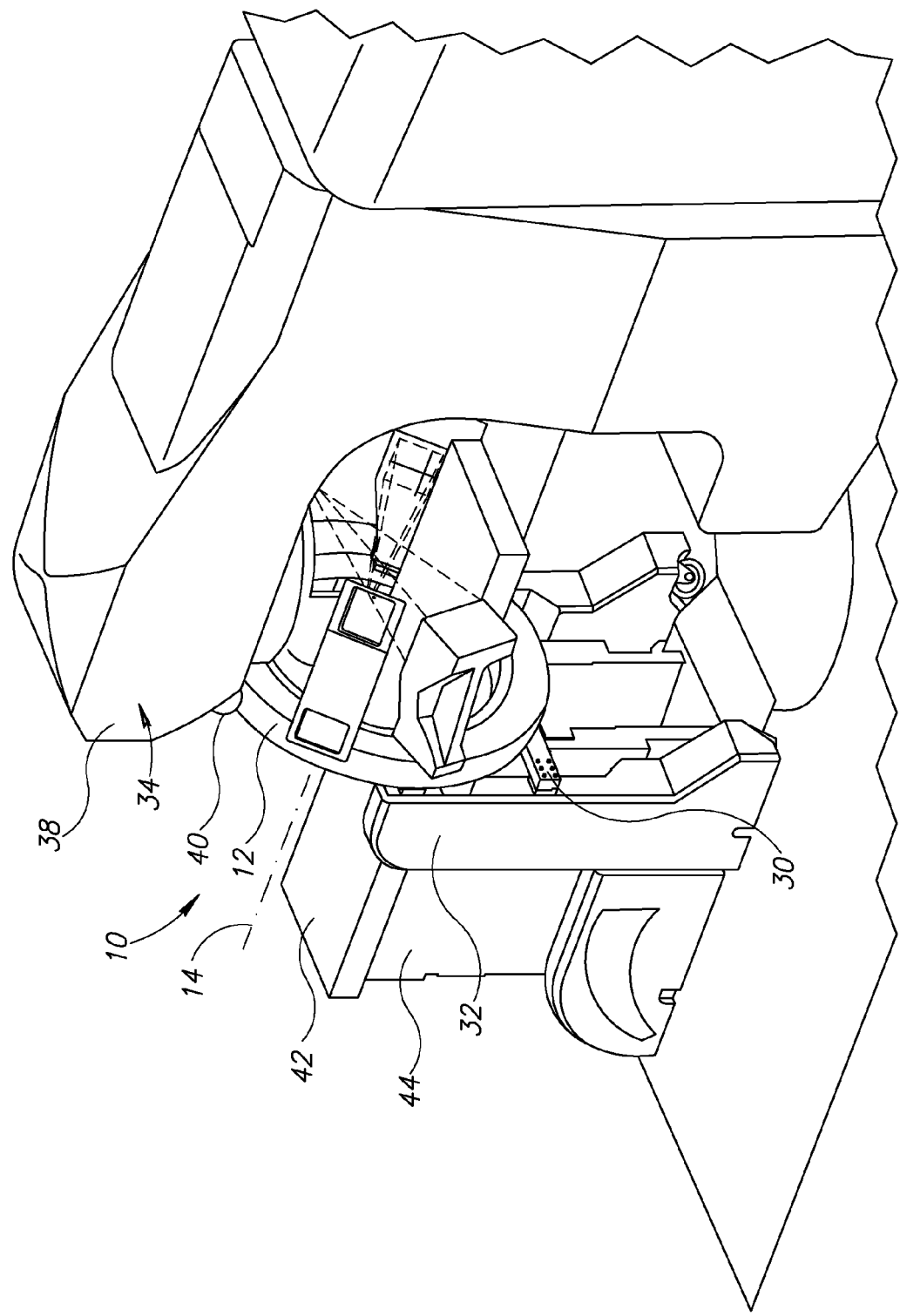
FIG. 4 is a simplified illustration of the CT scanning system of FIG. 1 coupled to a rotating gantry and treatment device, in accordance with an embodiment of the present invention.

Reference is now made to FIG. 4. The CT scanning system 10 may be coupled to a treatment device 34, such as a LINAC device, by means of a treatment device coupler 36. The treatment device coupler 36 couples the coordinate system of the treatment device 34 to the coordinate system of CT scanning system 10. The treatment device 34 may include a rotating gantry 38. A gantry coupler 40 may cause rotation of the gantry 12 of CT scanning system 10 by coupling gantry 12 to the rotating gantry 38 of treatment device 34.

A couch 42 may be provided for the object to lie on. The couch 42 may cause translation of the object (e.g., patient) as controlled by a translation controller 44. The object may be translated during rotation of the gantry, and may be generally parallel to the rotation axis 14.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A computerized tomography (CT) scanning system comprising:

a gantry operable to rotate about a rotation axis; and first and second X-ray imagers mounted on said gantry, each X-ray imager comprising a radiation source and a detector, wherein said radiation source is operative to emit a radiation beam and said detector is positioned to receive said radiation beam so as to acquire partial projection sets of an object through which said beams pass, wherein a union of said partial projection sets forms a projection set sufficient for CT reconstruction of said object;

wherein the radiation source and the detector of each of said X-ray imagers are aligned off-axis with respect to an isocenter lying on said rotation axis, wherein each of said radiation beams comprise a cone beam, and wherein a periphery of the cone beam of the first X-ray imager intersects the isocenter and extends to a first radius outwards from the isocenter and said rotation axis thereby defining an inner circle, and wherein a periphery of the cone beam of the second X-ray imager is tangent to said inner circle and the periphery of the cone beam of the second X-ray imager extends to a second radius outwards from the isocenter and said rotation axis thereby defining an outer circle;

and wherein said partial projection sets comprise projections of axial cylindrical object shells, wherein said axial cylindrical object shells are bound by an innermost shell, defined by the periphery of the cone beam of the first X-ray imager that extends to the inner circle relative to the rotation axis, and by an outermost shell, defined by the periphery of the cone beam of the second X-ray imager that extends to the outer circle relative to the rotation axis.

2. The CT scanning system according to claim 1, wherein at least one of said partial projection sets overlaps part of another one of said partial projection sets.

3. The CT scanning system according to claim 1, wherein said gantry comprises a rotator and a controller operable to control rotation of said rotator.

4. The CT scanning system according to claim 3, further comprising a treatment device coupler operable to couple a coordinate system of a treatment device to a coordinate system of said CT scanning system.

5. The CT scanning system according to claim 1, wherein said gantry comprises a gantry coupler operable to cause rotation of said gantry by coupling said gantry to a rotating gantry of a treatment device.

6. The CT scanning system according to claim 5, wherein said treatment device comprises at least one of a linear accelerator, a cobalt radiotherapy unit, surgical and electrosurgical units, a focused ultrasound treatment unit, a shockwave unit, a biopsy device, a coagulation device, and a radiation emitting device.

7. The CT scanning system according to claim 1, further comprising a couch operable to cause translation of said object.

8. The CT scanning system according to claim 7, further comprising a translation controller operable to control translation of said object.

9. The CT scanning system according to claim 8, wherein said translation controller is further operable to cause translation of said object during rotation of said gantry.

10. The CT scanning system according to claim 8, wherein said translation of said object is generally parallel to said rotation axis.

11. A method for computerized tomography (CT) scanning comprising:
using the CT scanning system of claim 1 to emit radiation beams from the plurality of radiation sources mounted on said gantry; and
detecting said radiation beams with said detectors positioned to receive said radiation beams, so as to acquire partial projections set of an object through which said beams pass, wherein a union of said partial projections sets forms a projection set sufficient for CT reconstruction of said object.

12. The method according to claim 11, further comprising rotating said gantry and repeating the steps of emitting and detecting the radiation beams.

13. The CT scanning system according to claim 1, wherein said isocenter is at an origin of upper and lower horizontal and vertical axes, and the radiation source of said first X-ray imager is positioned about 55° counterclockwise from the upper vertical axis, the detector of said first X-ray imager is positioned about 55° counterclockwise from the lower vertical axis, the radiation source of said second X-ray imager is positioned about 70° clockwise from the upper vertical axis and the detector of said second X-ray imager is positioned about 70° clockwise from the lower vertical axis.

* * * * *